(12) United States Patent
Nakagata et al.

(10) Patent No.: US 10,500,275 B2
(45) Date of Patent: Dec. 10, 2019

(54) SUPEROVULATION IN MICE COMPRISING ADMINISTRATION OF ANTI-INHIBIN SERUM AND EQUINE CHORIONIC GONADOTROPIN

(71) Applicant: NATIONAL UNIVERSITY CORPORATION KUMAMOTO UNIVERSITY, Kumamoto (JP)

(72) Inventors: Naomi Nakagata, Kumamoto (JP); Toru Takeo, Kumamoto (JP)

(73) Assignee: National University Corporation Kumamoto University, Kumamoto (JP)

( * ) Notice: Subject to any disclaimer, the term of this patent is extended or adjusted under 35 U.S.C. 154(b) by 50 days.

(21) Appl. No.: 15/552,257

(22) PCT Filed: Feb. 19, 2016

(86) PCT No.: PCT/JP2016/054838
§ 371 (c)(1),
(2) Date: Dec. 29, 2017

(87) PCT Pub. No.: WO2016/133195
PCT Pub. Date: Aug. 25, 2016

(65) Prior Publication Data
US 2018/0104333 A1    Apr. 19, 2018

(30) Foreign Application Priority Data

Feb. 20, 2015  (JP) ................................ 2015-032354
Apr. 30, 2015  (JP) ................................ 2015-092485

(51) Int. Cl.
| | | |
|---|---|---|
| *A61K 39/395* | (2006.01) |
| *A01K 67/02* | (2006.01) |
| *A61K 9/00* | (2006.01) |
| *A61K 38/22* | (2006.01) |
| *A61P 5/24* | (2006.01) |
| *A01K 67/027* | (2006.01) |

(52) U.S. Cl.
CPC .......... *A61K 39/3955* (2013.01); *A01K 67/02* (2013.01); *A61K 9/0019* (2013.01); *A61K 38/22* (2013.01); *A61P 5/24* (2018.01); *A01K 67/0275* (2013.01); *A01K 2227/105* (2013.01)

(58) Field of Classification Search
None
See application file for complete search history.

(56) References Cited

U.S. PATENT DOCUMENTS

| | | |
|---|---|---|
| 9,453,242 B2 | 9/2016 | Nakagata et al. |
| 2003/0237104 A1 | 12/2003 | Nomura |
| 2012/0278911 A1 | 11/2012 | Choi et al. |
| 2013/0276159 A1 | 10/2013 | Nakagata et al. |
| 2017/0037433 A1 | 2/2017 | Nakagata et al. |

FOREIGN PATENT DOCUMENTS

| | | |
|---|---|---|
| JP | 3091415 B2 | 7/2000 |
| JP | 2005530509 A | 10/2005 |
| JP | 2006204180 A | 8/2006 |
| WO | 2012036107 A1 | 3/2012 |

OTHER PUBLICATIONS

The website downloaded from <www.sciencedaily.com/releases/2015/06/150619103353.htm>, "Successful ovulation of 100 eggs from one female mouse." ScienceDaily. ScienceDaily, Jun. 19, 2015 (Year: 2015).*
Fowler and Edwards, J Endocrin. 1957; 15: 374-384 (Year: 1957).*
Sato and Mars, Journal of in vitro Fertilization and Embryo Transfer, 1986; 3: 353-357 (Year: 1986).*
T. Takeo, et al., "Methyl-Beta-cyclodextrin Improves Fertilizing Ability of C57BL/6 Mouse Sperm After Freezing And Thawing By Facilitating Cholesterol Efflux From The Cells", Biology of Reproduction, 2008, vol. 78, pp. 546-551.
T. Takeo, et al., "Reduced Glutathione Enhances Fertility of Frozen/Thawed C57BL/6 Mouse Sperm After Exposure To Methyl-Beta-Cyclodextrin", Biology of Reproduction, 2011, vol. 85, pp. 1066-1072.
M. Yokoyama, et al., "Number of Spontaneous And Induced Ovulation in Various Strains of Mice", J.Mamm.Ova Res., 1989, vol. 6(2), pp. 151-155.
S.L. Byers, et al., Performance Of Ten Inbred Mouse Strains Following Assisted Reproductive Technologies (ARTs), Theriogenology, 2006, vol. 65, pp. 1716-1726.
H. Kishi, et al., "Induction Of Superovulation by Immunoneutralization Of Endogenous Inhibin Through The Increase In The Secretion Of Follicle-Stimulating Hormone In The Cyclic Golden Hamster", Endocrinology, 1996, vol. 151, pp. 65-75.
C. Rivier, et al., "Immunoneutrazlization Of Endogenous Inhibin Modifies Hormone Secretion And Ovulation Rate In The Rat", Endocrinology, 1989, vol. 125, pp. 152-157.
F. Shi, et al., "Induction Of Superovulation By Inhibin Vaccine In Cyclic Guinea-Pigs", Journal of Reproduction and Fertility, 2000, vol. 118, pp. 1-7.
S. Akagi, et al., "Ovarian Response And FSH Profile In Cows Following Injection Of Various Doses Of Inhibin Antiserum", The Journal of Veterinary Medical Science, 1997, vol. 59, pp. 1129-1135.

(Continued)

*Primary Examiner* — Christina M Borgeest
(74) *Attorney, Agent, or Firm* — Hunton Andrews Kurth LLP

(57) ABSTRACT

An object of the present invention is to provide a novel method that is excellent in superovulation induction efficiency. Specifically, it is an object to provide a method giving superior superovulation induction efficiency as compared with conventional methods using equine chorionic gonadotropin (eCG) and human chorionic gonadotropin (hCG). The present invention provides a superovulation inducing method, comprising simultaneously administering anti-inhibin antibody and equine chorionic gonadotropin (eCG), then, administering human chorionic gonadotropin (hCG), to a female mouse.

14 Claims, 6 Drawing Sheets

(56) References Cited

OTHER PUBLICATIONS

Y. Nambo, et al., "Effect Of Passive Immunization Against Inhibin On FSH Secretion, Folliculogenesis And Ovulation Rate During The Follicular Phase Of The Estrous Cycle In Mares", Theriogenology, 1998, vol. 50, pp. 545-557.
H. Wang, et al., "Superovulation, Fertilization And In Vitro Embryo Development In Mice After Administration Of An Inhibin-Neutralizing Antiserum", 2001, vol. 122, pp. 809-816.
M.S. Medan, et al., "Immunization Against Endogenous Inhibin Increases Normal Oocyte/Embryo Production In Adult Mice", Endocrine, 2004, vol. 24(2), pp. 115-119.
A. Hasegawa, et al., "Efficient Production Of Offspring From Japanese Wild-Derived Strains Of Mice (*Mus Musculus molossinus*) By Improved Assisted Reproductive Technologies", 2012, vol. 86(5):167, pp. 1-7.
K. Mochida, et al., "Devising Assisted Reproductive Technologies For Wild-Derived Strains Of Mice: 37 Strains From Five Subspecies of *Mus musculus*", PLOS ONE, 2014, vol. 9(12): e114305.
K. Nakao, et al., "Simple And Efficient Vitrification Procedure For Cryopreservation Of Mouse Embryos", 1997, vol. 46 (3), pp. 231-234.
N. Nakagata, "Embryo Transfer Through The Wall Of The Fallopian Tube In Mice", Exp. Anim., 1992, vol. 41(3), pp. 387-388.
Extended European Search Report dated Aug. 27, 2018 for European Application No. 16752581.5.
Toru, Takeo et al., "Superovulation Using the Combined Administration of inhibin Antiserum and Equine Chorionic Gonadotropin Increases the Number of Ovulated Oocytes in C57BL/6 Female Mice," PLOS ONE, vol. 10, No. 5., pp. 1-11, May 29, 2015.

\* cited by examiner

SUPEROVULATION IN MICE COMPRISING ADMINISTRATION OF ANTI-INHIBIN SERUM AND EQUINE CHORIONIC GONADOTROPIN

CROSS REFERENCE TO RELATED APPLICATIONS

This application is a National Stage application from PCT/JP2016/054838 filed Feb. 19, 2016, which claims Priority to Japanese Patent application 2015-032354 filed Feb. 20, 2015 and Japanese Patent application 2015-092485 filed Apr. 30, 2015.

FIELD OF THE INVENTION

The present invention relates to a method of inducing superovulation of a female mouse.

BACKGROUND OF THE INVENTION

Experimental animals are indispensable in studies to deeply understand healthy or pathological conditions and to evaluate the efficacy of a candidate treatment targeting application to human diseases. Mice are the experimental animals used most commonly in life science studies. Recently, there are a lot of genetically engineered mouse strains that have been produced to decipher the function of genes as life phenomena and disease models.

A great number of genetically engineered mice are preserved in mouse resource banks, and they are available using the website of International Mouse Strain Resource (IMSR). In mouse resource banks, various reproductive techniques are used, and genetically engineered mice are preserved, transported or produced in an efficient way. To date, an efficient mouse resource bank system is constructed by cryopreservation of sperm, oocytes/ova (hereinafter collectively called "ova") and embryos of a genetically engineered mouse. Sperm, ova and embryos cryopreserved in mouse resource banks can be easily transported to researchers in need of a genetically engineered mouse by using courier services.

In addition, the present inventors developed a novel technique for conveniently transporting non-frozen mouse embryos or sperm at 4° C. Owing to this technique, special techniques and insulating containers (dryshippers) handling cryopreserved samples became unnecessary. Further, the present inventors developed an in vitro fertilization system using methyl-β-cyclodextrin (MBCD) and reduced glutathione (GSH) (Non-Patent document 1, Non-Patent document 2, Patent document 1, Patent document 2). This technique supports use in medicinal and pharmaceutical fields. Such an in vitro fertilization method can stably attain high fertilization rate using cryopreserved or refrigerated mouse sperm. An improvement in the reproductive techniques is extremely important for carrying out a study efficiently using a genetically engineered mouse.

The phenomenon of superovulation includes follicular maturation and induction of ovulation due to hormonal administration. Superovulation is generally utilized for producing a genetically engineered mouse using various reproductive techniques, and is routinely used for obtaining ova from oocyte/ovum (hereinafter collectively called "ovum") donors prior to in vitro fertilization (IVF). In superovulation of a mouse, administration of equine chorionic gonadotropin (eCG) promotes growth of a follicle and administration of human chorionic gonadotropin (hCG) induces ovulation. In general, equine chorionic gonadotropin (eCG) stimulating growth of a follicle is administered intraperitoneally to a female mouse, then, human chorionic gonadotropin (hCG) inducing ovulation is injected intraperitoneally (for example, Patent document 3). Equine chorionic gonadotropin (eCG) is one of gonadotropic hormones and called also PMSG, and manifests an action like follicle stimulating hormone (FSH) which is likewise one of gonadotropic hormones. The number of ovulated ova in a C57BL/6 strain which is usually used as the background of a genetically engineered mouse is usually about 9 per female mouse, while it becomes about 25 by a superovulation treatment using eCG and hCG (Non-Patent document 3, Non-Patent document 4).

Administration of inhibin antiserum (IAS) is reported to increase the number of ovulated ova in various animals such as, for example, hamsters, rats, guinea pigs, cows, mares and the like similar to other superovulation treatments (Non-Patent document 5, Non-Patent document 6, Non-Patent document 7, Non-Patent document 8, Non-Patent document 9, Patent document 4). Inhibin is known as a hormone which is secreted from a granulosa cell in the ovarian follicle. Inhibin secreted into the general circulation and acts on the anterior pituitary gland, thereby inhibiting secretion of follicle stimulating hormone (FSH) from the gland. Administration of inhibin antiserum to female rats neutralizes the function of inhibin, resulting in negating negative feedback to FSH by inhibin, and promotes growth of a follicle and the number of ovulated ova in the rat.

It is reported that inhibin antiserum increased the number of ovulated ova in a ddY strain female mouse (Non-Patent document 10, Non-Patent document 11). The effect of inhibin antiserum (IAS) is reported also in a wild-derived strain female mouse (Non-Patent document 12). Immunity neutralization of endogenous inhibin by IAS is an effective strategy for inducing superovulation in a mouse by suppressing negative feedback, thereby increasing endogenous FSH.

Wang et al. first reported that administration of 200 μL of IAS instead of eCG increased the number of ovulated ova in ddY strain immature mice and adult mice. Medan et al. reported that the concentration of FSH in plasma increased remarkably in a ddY strain female mouse treated with IAS. An increase in FSH contributes to promote growth of a follicle and to increase the number of ovulated ova.

Hasegawa et al. likewise report that 50 μL of IAS increases the number of ova in Japanese wild-derived strains (MSM/Ms and JF1/Ms) belonging to *Mus musculus molossinus* showing low responsiveness to eCG. It is known that for mice of most strains, about 20 to 40 ova can be obtained from one female mouse by promoting maturation of a lot of follicles by eCG having FSH-like action, then, inducing ovulation by hCG, while in many wild-derived mice, this system does not work well. Then, Hasegawa et al. succeeded in increasing the ovulation number of about 5 up to an average of 25 in wild-derived mice MSM/Ms and JF1/Ms by administering anti-inhibin antibody, thereby suppressing negative feedback, to increase endogenous FSH, supposing that the wild-derived mice do not respond to a hormone derived from another species, as one cause thereof.

As described above, the method using anti-inhibin antibody tries to increase the number of ovulated ova by increasing endogenous FSH, instead of excessively administering eCG having FSH-like action from outside (exogenous) to promote growth of a follicle. This would be effective particularly against wild-derived mice for which the remarkable effect is not obtained by eCG, as described above.

According to Hasegawa et al., the age in weeks of a female mouse most suitable for IAS administration is 5 to 7 weeks of age for MSM/Ms and JF1/Ms. Recently, Mochida et al. compared effects of eCG or IAS against the number of ovulated ova in various wild-derived strains from 5 subspecies of *Mus musculus* (Non-Patent document 13). The responsiveness to eCG or IAS was strong depending on the genetic background thereof. According to Mochida et al., a female mouse belonging to *Mus musculus molossinus* had a tendency of showing higher responsiveness to IAS as compared with eCG. In contrast, *Mus musculus domesticus* had a tendency of showing lower responsiveness to IAS as compared with eCG.

As described above, the effect of IAS is reported for some mouse strains, but there is no report on the effect of inhibin antiserum against a C57BL/6 strain mouse which is used most widely as an inbred mouse. This may be based on a fact that a C57BL/6 strain mouse shows high responsiveness to administration of eCG which is an exogenous gonadotropic hormone derived from another species. Further, the reason for this is that *Mus musculus domesticus* is believed to have lower responsiveness to inhibin antiserum (IAS) as compared with eCG, as described above, according to Mochida et al., and C57BL/6 being known to belong to *Mus musculus domesticus*.

The increase of ovulated ova by a superovulation treatment definitely decreases the number of ovum donors and raises the efficiency of animal production. In animal tests, it is important to minimize the number of animals based on the rule of 3 Rs (Reduction, Refinement and Replacement). Thus, it is strongly desired to develop a further efficient novel superovulation technique to increase the number of ovulated ova.

CITATION LIST

Patent Literature

[Patent Literature 1: Japanese Unexamined Patent Application Publication (Tokkai) No. 2016-204180
Patent Literature 2: WO 2012/036107
Patent Literature 3: Japanese Unexamined Patent Application Publication (Translation of PCT Application) (Tokuhyo) No. 2005-530509
Patent Literature 4: Patent Publication No. 3091415

Non-Patent Literature

Non-Patent Literature 1: Takeo et al., Biology of Reproduction 78: 546-551 (2008)
Non-Patent Literature 2: Takeo et al., Biology of Reproduction 85: 1066-1072 (2011)
Non-Patent Literature 3: Yokoyama et al., J. Mamm. Ova Res 6: 151-155 (1989)
Non-Patent Literature 4: Byers et al., Theriogenology 65: 1716-1726) (2006)
Non-Patent Literature 5: Kishi et al., The Journal of endocrinology 151: 65-75 (1996)
Non-Patent Literature 6: River et al., Endocrinology 125: 152-157 (1989)
Non-Patent Literature 7: Shi et al., Journal of reproduction and fertility 118: 1-7 (2000)
Non-Patent Literature 8: Akagi et al., The Journal of veterinary medical science/the Japanese Society of Veterinary Science 59: 1129-1135 (1997)
Non-Patent Literature 9: Nanbo et al., Theriogenology 50: 545-557 (1998)
Non-Patent Literature 10: Wang et al., Reproduction 122: 809-816 (2001)
Non-Patent Literature 11: Medan et al., Endocrine 24: 115-119 (2004)
Non-Patent Literature 12: Hasegawa et al., Biology of reproduction 86: 167, 161-167 (2012)
Non-Patent Literature 13: Mochida et al., PloS one 9: e114305 (2014)
Non-Patent Literature 14: Nakao et al., Experimental animals/Japanese Association for Laboratory Animal Science 46: 231-234 (1997)
Non-Patent Literature 15: Nakagata et al., Experimental animals/Japanese Association for Laboratory Animal Science 41: 387-388 (1992)

SUMMARY OF THE INVENTION

Technical Problem

As described above, a method of administering equine chorionic gonadotropin (eCG) followed by administration of human chorionic gonadotropin (hCG) and a method of using inhibin antiserum (IAS) instead of eCG are known as the superovulation treatment technique, however, there is a desire for a method giving better superovulation efficiency. In addition, a method using eCG and hCG is reported for a C57BL/6 strain mouse which is used most widely as an inbred mouse, however, there is no report on a further improved method, and it is reported that responsiveness to superovulation is low when IAS is used instead of eCG in an experiment using a mouse of *Mus musculus domesticus* to which the C57BL/6 strain belongs.

Therefore, a further method capable of efficiently inducing superovulation in a C57BL/6 mouse which is used most widely in the technical field of a genetically engineered mouse has been desired.

Solution to Problem

The present inventors have intensively studied to solve the above-described problem and resultantly found an effect by a combination (IASe) of IAS and eCG on the number of ovulated ova of a C57BL/6 strain immature female mouse in a superovulation treatment, completing the present invention. It is reported that a C57BL/6 strain mouse shows high responsiveness to administration of exogenous eCG having FSH-like action, and shows only low responsiveness to administration of inhibin antiserum increasing endogenous FSH, as compared with eCG. Surprisingly, however, a combination (IASe) of IAS and eCG induced remarkable superovulation.

Additionally, the present inventors have confirmed the quality of ova produced by superovulation using IASe, by in vitro fertilization (IVF) with sperm of a C57BL/6 mouse or a genetically engineered mouse, to find good quality. Further, the developing ability of the resultant embryo (fresh or cryopreserved thereafter) was confirmed by embryonic transplantation. As a result, also the developing ability was excellent.

The present invention includes the following embodiments.

(1) A superovulation inducing method, comprising simultaneously administering anti-inhibin antibody and equine chorionic gonadotropin (eCG), then, administering human chorionic gonadotropin (hCG), to a female mouse.

(2) The superovulation inducing method described in (1), wherein the anti-inhibin antibody is administered in the form of inhibin antiserum.

(3) The superovulation inducing method described in (1) or (2), wherein the female mouse is a 3 to 30-week old female mouse.

(4) The superovulation inducing method described in (3), wherein the female mouse is 3 to 5 weeks of age.

(5) The superovulation inducing method described in (3) or (4), wherein the female mouse is a C57BL/6 strain female mouse.

(6) The superovulation inducing method described in any one of (2) to (5), wherein the dosage of the inhibin antiserum is 0.4 mL or less.

(7) The superovulation inducing method described in (6), wherein the dosage of the inhibin antiserum is between 0.05 mL or more and 0.4 mL or less.

(8) The superovulation inducing method described in (6) or (7), wherein the dosage of the equine chorionic gonadotropin is between 1 IU or more and 10 IU or less.

(9) An in vitro fertilization method comprising
 a. a step of producing an ovum using the method described in any one of (1) to (8), and
 b. a step of fertilizing the ovum produced by the step and a sperm of a genetically engineered mouse.

(10) The in vitro fertilization method described in (9), wherein the sperm is a sperm derived from a C57BL/6 strain male mouse.

(11) An ovum produced by using the method described in any one of (1) to (8).

Effect of the Invention

The novel superovulation technique using combined administration of IAS and eCG according to the present invention can significantly increase the number of ovulated ova and can produce an extremely large number of ova from one female mouse, as compared with conventional methods using eCG.

DETAILED DESCRIPTION

[Mode for Carrying Out the Invention]

Figure 1:
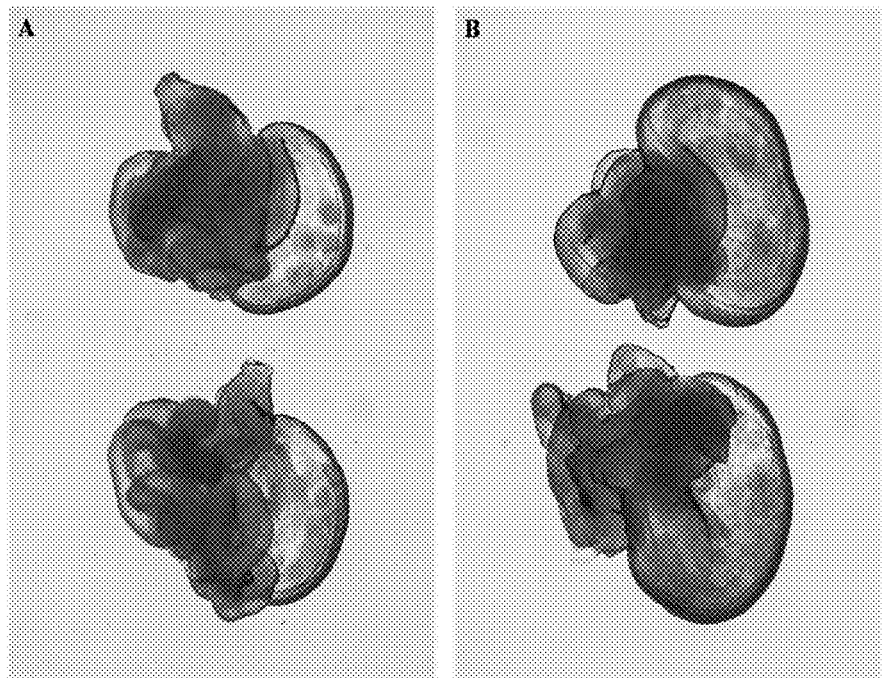
FIG. 1 is a photograph of observation of ampulla of oviduct after injection with 7.5 IU of eCG or IASe (0.1 mL of IAS and 3.75 IU of eCG), then, with hCG. A shows one with only eCG, and B shows one with IASe.

Hereinafter, the present invention will be illustrated and described in detail with reference to the exemplary embodiments, along with the preferred methods and materials which can be used in practice of the present invention. However, the present invention is not limited thereto.

Unless otherwise specified in the sentences, any technical terms and scientific terms used in the present specification, have the same meaning as those generally understood by those of ordinary skill in the art to which the present invention belongs. Any materials and methods equivalent or similar to those described in the present specification can be used for practicing the present invention.

All publications and patents cited herein in connection with the present invention described herein are incorporated herein by reference, for example, as indicating methodology, materials, etc. that can be used in the present invention.

The present inventors first found that responsiveness to IAS (0.1 or 0.2 mL) and responsiveness to eCG (7.5 IU) are equivalent in superovulation of a C57BL/6 strain female mouse. Further, the present inventors found that responsiveness to IAS and eCG is amplified remarkably by combined administration thereof. Administration of IASe increased the number of ovulated ova about 3-fold, as compared with administration of IAS or eCG alone. In in vitro fertilization using sperm of a C57BL/6 mouse, the ovum obtained by superovulation using IASe manifested usual development to a two-celled embryo. A fresh or cryopreserved embryo obtained by in vitro fertilization using ova of a C57BL/6 mouse and sperm of a genetically engineered mouse developed to an offspring as usual by embryonic transplantation.

The present invention will be illustrated in detail below.

The present invention is characterized in that superovulation is induced and the number of ovulated ova is increased by administering anti-inhibin antibody and equine chorionic gonadotropin (eCG) to an immature 3 to 30-week old female mouse, then, administering human chorionic gonadotropin (hCG) thereto.

Further, the present invention includes an ovum obtained as described above.

Furthermore, the present invention includes a method of fertilizing an ovum obtained by using the above-described superovulation induction method with fresh, refrigerated or cryopreserved mouse sperm to produce a two-celled embryo, and moreover, includes a two-celled embryo produced as described above.

Still further, the present invention includes a method of transplanting a two-celled embryo produced as described above, to produce an offspring, and moreover, includes a mouse produced as described above.

The female mouse strain used in the present invention is not particularly restricted, and includes, for example, BALB/c, C3H/He, C57BL/6J, C57BL/6N, DBA/2N, ICR, FVB/N, BDF1, B6CF3F1, 129T2/SvEmsJ, NOD, CBA/J, MSM/Ms, JF1/Ms, A/J, CD1 and the like, and preferable are C57BL strain mice, more preferable are C57BL/6 strain mice. The female mouse which can be used in the present invention may contain any mutation (for example, transgenic, knockout, knockin). In production of a mouse having a specific property, a mouse having any mutation according to the object can be used.

The age in weeks of the female mouse used in the present invention is 3 to 30 weeks of age, and it is preferably 3 to 20 weeks of age, more preferably 3 to 10 weeks of age, further preferably about 3 weeks of age to about 5 weeks of age, most preferably about 4 weeks of age. When a C57BL/6 strain mouse is used, it is particularly preferable to use an about 4-week old mouse, and an enormous number of ova can be produced by this.

The anti-inhibin antibody used in the present invention may be an antibody having an activity neutralizing endogenous inhibin of a mouse. For example, inhibin antiserum containing anti-inhibin antibody can be obtained by immunizing a castrated goat using purified 32 kDa porcine or mouse inhibin as an antigen. The anti-inhibin activity can be measured by an ordinary method. For example, immune titer can be measured by an immunoassay method. In the present invention, the anti-inhibin antibody may be inhibin antiserum or in the form of purified antibody (including partially purified antibody).

When inhibin antiserum is used, for example, 0.05 mL to 0.5 mL, preferably 0.05 mL to 0.4 mL, more preferably 0.1 mL to 0.2 mL of the antiserum prepared is administered to a mouse, though the dosage is not limited to this range.

The amount of equine chorionic gonadotropin (eCG) to be administered to a female mouse in the superovulation inducing method of the present invention is an amount usually used in a superovulation treatment for an experimental mouse. For example, it is usually 1 to 15 IU, preferably 1 to 10 IU, more preferably 1.5 to 10 IU, further preferably 1.5 to 8 IU. In the case of about 3 to about 5-week old, more preferably about 4-week old C57BL/6 strain mice, particularly excellent superovulation induction can be attained by using 1.5 to 8 IU of eCG in combination with IAS.

The amount of human chorionic gonadotropin (hCG) to be administered to a female mouse in the superovulation inducing method of the present invention is an amount usually used in a superovulation treatment for an experimental mouse. It is, for example, 1 to 15 IU, preferably 1.5 to 10 IU, further preferably 1.5 to 8 IU.

The superovulation inducing method of the present invention is characterized by administering anti-inhibin antibody (for example, inhibin antiserum) and equine chorionic gonadotropin (eCG) simultaneously to an immature female mouse, then, administering human chorionic gonadotropin (hCG) to the mouse.

The anti-inhibin antibody and eCG may be administered at the same time or separately (approximately) at the same time, or may be administered together as a mixture. Administration can be carried out, for example, by intraperitoneal injection, though the method is not limited to this. After a certain period of time, for example, 48 hours after, hCG is administered. Administration of hCG can be carried out, for example, by intraperitoneal injection, though the method is not limited to this.

When the superovulation inducing method of the present invention is used, an enormous number of ova can be obtained as compared with the number of ova obtained in usual ovulation. For example, when the method of the present invention is used for a C57BL/6 strain mouse, 80 or more ova can be usually obtained, and in the optimum case, over 100 ova can also be obtained, from one female mouse. Also thus obtained ovum is included in the present invention.

The ovum obtained by the present invention can be fertilized with sperm of a male mouse and used. Sperm can be collected form an adult male mouse by an ordinary method, and in the fresh state or after refrigeration or cryopreservation, the sperm can be fertilized with an ovum produced in the present invention. Fertilization can be conducted according to an ordinary method. For example, fertilization can be conducted according to methods reported by the present inventors (Non-Patent documents 1 and 2). The fertilized ovum obtained from the ovum produced in the present invention can develop successfully to a two-celled embryo. For example, when the method of the present invention is used for a C57BL/6 strain female mouse, usually about 80% or more of fertilized ova, and in a preferable case, about 90% or more of fertilized ova can develop to a two-celled embryo. Thus obtained two-celled embryo can also be cryopreserved. Also thus obtained fresh or cryopreserved two-celled embryo is included in the present invention.

Further, it is also possible to produce an offspring by transporting a two-celled embryo obtained by using an ovum produced by the method of the present invention to a recipient by embryonic transplantation. Embryonic transplantation can be conducted by an ordinary method. Also thus produced mouse is included in the present invention.

EXAMPLES

The present invention will be illustrated specifically by examples below, but the present invention is not limited to the following examples.

1. Material and Method (1-1) Animal

Female and male mice of C57BL/6 strain and female mice of other strains were purchased from CLEA Japan, Inc. In usual experiments, mice of 4 weeks of age were used as an ovum donor and mice of 12 weeks of age were used as sperm donor. In experiments for examining the age in weeks of a mouse as an ovum donor, female mice of described weeks of age were used. Three strains of genetically engineered mice of the C57BL/6 background were used in the same way as sperm donor at 12 weeks of age. ICR mice were used as a recipient of a two-celled embryo at 8 to 16 weeks of age. All animals were allowed to take meals and water freely and housed at 22° C.±1° C. under 12-hour light-dark cycle (illumination time: 7:00 to 19:00). Animal tests followed the protocol for animal experiments approved by the Animal Care and Use Committee of Kumamoto University School of Medicine.

(1-2) Medium

Sperms were preincubated in a modified Krebs-Ringer sodium bicarbonate buffer (TYH) containing 1.0 mg/mL polyvinyl alcohol and 0.75 mM methyl-β-cyclodextrin (Sigma-Aldrich). Calcium-enhanced human tubal fluid (mHTF) was used as a fertilization medium. Potassium simplex optimization medium (KSOM) was used for operation of a two-celled embryo and for culture up to blastocyst-stage embryo. Cryopreservation of an embryo was conducted using 1 M dimethyl sulfoxide (DMSO) diluted with modified phosphate buffer (PB1), PB1 containing 2 M DMSO, 1 M acetamide and 3 M propylene glycol (DAP213). A vitrified embryo was warmed in PB1 containing 0.25 M sucrose.

(1-3) Ovulation and Collection of Ovum

A female mouse was administrated IAS (0.05 to 0.4 mL) alone, eCG (1.875 IU to 15 IU, ASKA Pharmaceutical Co., Ltd.) alone, or IAS and eCG in combination. IAS was prepared by using a mouse inhibin peptide, according to a method described in a paper of Kishi et al. (Non-Patent document 5, incorporated herein as part of the present specification), and the antiserum prepared was used as it was. The antibody activity of IAS prepared was measured using an ELISA method, and if necessary, the IAS was standardized before use. Specifically, a 5 μg/mL mouse inhibin peptide was adsorbed onto a plate for ELISA, then, washing and blocking were performed. Inhibin antiserum diluted 1000-fold to 128000-fold was treated, ELISA was conducted using anti-goat IgG antibody labeled with horseradish peroxidase as a secondary antibody, and it was confirmed that the inhibin antibody could be detected sufficiently even at maximum dilution ratio, and it was used in the following experiment.

Forty-eight hours after administration of these reagents GAS alone, eCG alone, or a combination of IAS and eCG), 7.5 IU of hCG (ASKA Pharmaceutical Co., Ltd.) was administered to a mouse. Seventeen hours after administration of hCG, the mouse was sacroficed by cervical dislocation, the oviduct of the mouse was collected quickly, and transferred to a fertilization dish covered with paraffin oil. Under microscopic observation, cumulus-oocyte complexex (COC) were collected from the oviduct, and transferred to a 200 μL drop of fertilization medium (female/drop). For each group, the number of ovulated ova and the fertilization ability of ova were examined.

(1-4) In Vitro Fertilization

Sperm were collected as described below from a genetically engineered mouse of C57BL/6 or C57BL/6 background. A male mouse was sacrificed by cervical dislocation, then, cauda epididymides was collected, and transferred to a dish of sperm preincubation medium covered with paraffin oil. Clots of sperm were collected from the cauda epididymides using a dissecting needle, and transferred to a 100 μL drop of the sperm preincubation medium. Sperm were preincubated for 60 minutes, to induce capacitation. The preincubated sperm were added to a drop of the fertilization medium containing COC, and ova were cultured at 37° C. in atmosphere containing 5% $CO_2$ for 3 hours. The final concentration of motile sperms in the fertilization medium was 400 to 800 sperm/μL. At 3 hours after insemination, ova were washed in three drops of mHTF (80 μL). After washing of ova, the number of ova was counted. Twenty-four hours after insemination, the fertilization rate was calculated by dividing the total number of two-celled embryos by the total number of inseminated ova, then, multiplying the quotient by 100.

(1-5) Vitrification and Warming of Embryo

The procedure of embryo vitrification followed a report of Nakao et al. (Non-Patent document 14, incorporated herein as part of the present specification). After in vitro fertilization, two-celled embryos of a genetically engineered mouse were placed into a drop of DMSO solution (about 100μ), then, transferred to other drops of DMSO solution. An aliquot of 5 μL of the DMSO solution containing the embryos was placed in a cryogenic tube, and equilibrated at 0° C. for 5 minutes. Further, an aliquot of 45 μL DAP213 (2 M dimethyl sulfoxide, 1 M acetamide, 3 M propylene glycol solution) was added, and after equilibration for 5 minutes, and the cryogenic tube containing the embryos was immersed in liquid nitrogen, and preserved. The vitrified embryos in the cryogenic tube were warmed by adding 0.9 mL sucrose solution previously warmed at 37° C. The vitrified warmed embryos were collected from the sucrose solution, then, transferred into a drop of KSOM (100 μL). Ten minutes after, the number of morphologically normal embryos was counted before embryo transfer, to determine the survival rate.

(1-6) Embryo Transfer

Embryo transfer was conducted according to a procedure reported previously by the present inventors (Non-Patent document 15, incorporated herein as part of the present specification). Freshly collected or vitrified-warmed two-celled embryos of a genetically engineered mouse were transferred into the oviduct of an ICR female mouse (8 to 11 embryos/oviduct) on the day of observation of a vaginal plug (on Day 1 of pseudo-pregnancy). The embryos were transferred through the wall of the fallopian tube. The number of offspring was recorded 19 days after.

(1-7) Statistical Treatment

Statistical analysis was conducted using Prism version 5.0 (GraphPad). The result is expressed as average±standard deviation (SD). The results of groups were compared using analysis of variance after arcsine transformation of the percentages. $p<0.05$ was considered statistically significant.

2. Experiment (2-1) Combined Administration of IAS and eCG

Three kinds of administrations (IAS alone, eCG alone, and IASe (combination of IAS and eCG)) were conducted, and the ability of inducing superovulation was examined. Photographs observing ampulla of oviduct after injection with 7.5 IU of eCG or IASe (0.1 mL of IAS and 3.75 IU of eCG), then, with hCG, are shown in FIG. 1. The numbers of the resultant ova are shown in Table 1.

TABLE 1

| IAS (mL) | eCG (IU) | Total no. of ovulated oocytes | Average no. of oocytes/female | No. of two-cell embryos | Fertilization rate (%) |
|---|---|---|---|---|---|
| 0.1 | 0 | 321 | 32.1 ± 16.6 [c] | 310 | 96.6 ± 3.0 |
| 0.2 | 0 | 365 | 36.5 ± 12.5 [c] | 342 | 93.7 ± 4.7 |
| 0 | 3.75 | 87 | 8.7 ± 1.7 [a,b] | 84 | 96.6 ± 15.8 |
| 0 | 7.5 | 277 | 27.7 ± 5.4 [c] | 267 | 96.4 ± 3.2 |
| 0.1 | 3.75 | 1072 | 107.2 ± 22.7 [a,b,c,d] | 963 | 89.8 ± 3.7 |

Ten female mice were used as an ovum donor in each group. The result is expressed as average±standard deviation. "a" denotes P<0.05 as compared with 0.1 mL of IAS, "b" denotes P<0.05 as compared with 0.2 mL of IAS, "c" denotes P<0.05 as compared with 3.75 IU of eCG and "d" denotes P<0.05 as compared with 7.5 IU of eCG.

IASe (combination of 0.1 mL of ISA and 3.75 IU of eCG) increased most effectively the number of ovulated ova as compared with IAS alone or eCG alone. The number of ovulated ova by administration of IASe was about 3-fold of the number induced by administration of 0.2 mL of IAS or 7.5 IU of eCG. The effect of 0.1 or 0.2 mL of IAS was the same as the effect of 7.5 IU of eCG. That is, combined administration of IAS and eCG increased the number of ovulated ova in a C57BL/6 female mouse.

(2-2) Production of Two-celled Embryo from Ovum

Figure 2:
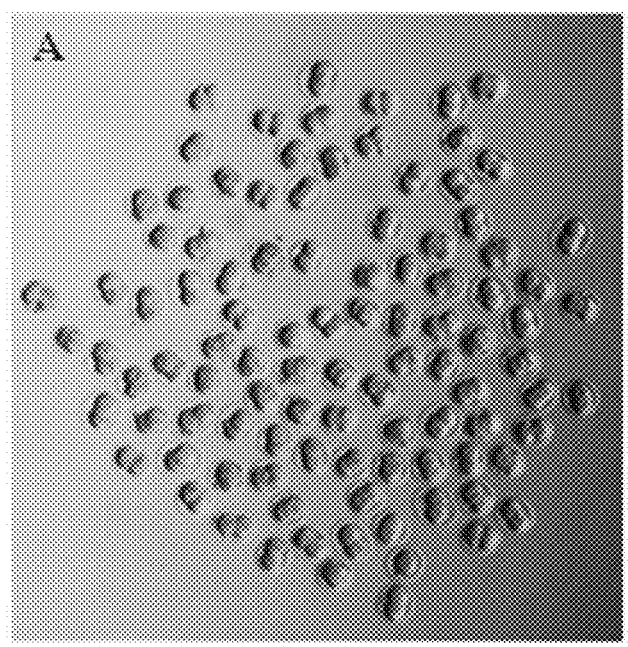
FIG. 2 is a photograph showing production of two-celled embryos from one female mouse showing superovulation induced by administering IASe (0.1 mL of IAS and 3.75 IU of eCG) followed by administration of hCG.

The embryo production efficiency between an ovum derived from a C57BL/6 female mouse which received IASe and sperm of a genetically engineered mouse was evaluated. IVF was performed using genetically engineered mice of 3 strains as sperm donors, and the ovum was developed to a two-celled embryo. The photograph of two-celled embryos is shown in FIG. 2. The results of the embryo production efficiency are shown in Table 2.

Superovulation was induced using IASe (0.1 mL of IAS and 3.75 IU of eCG). IASe were administered to two female mice in each mouse strain (ID of C57BL/6 female mouse: 7-12). As a control, superovulation was induced using six female mice with 7.5 IU of eCG (ID of C57BL/6 female mouse: 1-6). IVF was performed between ova of a C57BL/6 mouse and sperm of a genetically engineered mouse. As sperm donor, genetically engineered mice of three strains (A, B or C) were used.

TABLE 2

| Treatment | Oocyte donor ID | Sperm donor | No. of ovulated oocytes | No. of 2-cell embryos | Fertilization rate (%) |
|---|---|---|---|---|---|
| eCG | 1 | C57BL/6 | 35 | 35 | 100 |
|  | 2 |  | 36 | 36 | 100 |
|  | 3 |  | 30 | 30 | 100 |
|  | 4 |  | 38 | 37 | 97.4 |
|  | 5 |  | 36 | 35 | 97.2 |
|  | 6 |  | 42 | 41 | 97.6 |
|  | Average |  | 36.2 ± 3.9 | 35.7 ± 3.6 | 98.6 ± 1.4 |
| IASe | 7 | Strain A | 107 | 101 | 94.4 |
|  | 8 |  | 115 | 112 | 97.4 |
|  | 9 | Strain B | 110 | 106 | 96.4 |
|  | 10 |  | 110 | 104 | 94.5 |
|  | 11 | Strain C | 111 | 99 | 89.2 |
|  | 12 |  | 100 | 86 | 86 |
|  | Average |  | 108.8 ± 5.0* | 101.3 ± 8.8* | 93.1 ± 4.9* |

The result is expressed as average±standard deviation. * denotes P<0.05 as compared with eCG.

As shown in Table 2, over 100 ova were obtained from one female mouse by IASe treatment. The ovulated ova were subjected to usual fertilization with sperm of a genetically engineered mouse by IVF. As a result, two-celled embryos of a genetically engineered mouse were produced from superovulated ova using IASe. The resultant embryos were transplanted to a recipient, before or after cryopreservation by the following experiment.

(2-3) Production of Offspring

The developing ability of fresh or cryopreserved two-celled embryos produced by IVF between a C57BL/6 female mouse and a genetically engineered male mouse was confirmed by embryonic transplantation.

After conducting IVF between ova of a C57BL/6 female mouse and sperms of a genetically engineered male mouse, two-celled embryos having undergone no cryopreservation (ID of female mouse; eCG: 1-3, IASe: 7, 9, 11) or having undergone cryopreservation (ID of female mouse; eCG: 4-6, IASe: 8, 10, 12) were used in transplantation. The results are shown in Table 3.

TABLE 3

| Embryos | | Oocyte donor ID | No. of cryopreserved embryos | No. of recovered embryos | No. of survived embryos | No. of recipients | No. of transferred embryos | No. of offspring | |
|---|---|---|---|---|---|---|---|---|---|
| Fresh | eCG | 1 | — | — | — | 2 | 35 | 18 | 51.4 |
|  |  | 2 | — | — | — | 2 | 36 | 15 | 41.7 |
|  |  | 3 | — | — | — | 2 | 30 | 11 | 36.7 |
|  |  | Average | — | — | — | 2 | 33.7 ± 3.2 | 14.7 ± 3.5 | 43.6 ± 7.5 |
|  | IASe | 7 | — | — | — | 5 | 101 | 59 | 58.4 |
|  |  | 9 | — | — | — | 5 | 106 | 48 | 45.3 |
|  |  | 11 | — | — | — | 5 | 99 | 41 | 41.4 |
|  |  | Average | — | — | — | 5 | 102 ± 3.6* | 49.3 ± 9.1* | 48.4 ± 8.9 |
| Cryopreserved | eCG | 4 | 37 | 37 | 32 | 2 | 32 | 17 | 53.1 |
|  |  | 5 | 35 | 33 | 27 | 2 | 27 | 16 | 59.3 |
|  |  | 6 | 41 | 41 | 39 | 2 | 39 | 12 | 30.8 |
|  |  | Average | 37.7 ± 3.1 | 37.0 ± 4.0 | 32.7 ± 6.0 | 2 | 32.7 ± 6.0 | 15 ± 2.6 | 45.9 ± 15.0 |
|  | IASe | 8 | 112 | 111 | 100 | 5 | 100 | 51 | 51 |
|  |  | 10 | 104 | 101 | 84 | 5 | 84 | 32 | 38.1 |
|  |  | 12 | 86 | 85 | 85 | 5 | 85 | 35 | 41.2 |
|  |  | Average | 100.7 ± 13.3* | 99.0 ± 13.1* | 89.7 ± 9.0* | 5 | 89.7 ± 9.0* | 39.3 ± 10.2* | 43.9 ± 10.2 |

The result is expressed as average±standard deviation. * denotes P<0.05 as compared with eCG of each group of fresh or cryopreserved ova.

Figure 3:
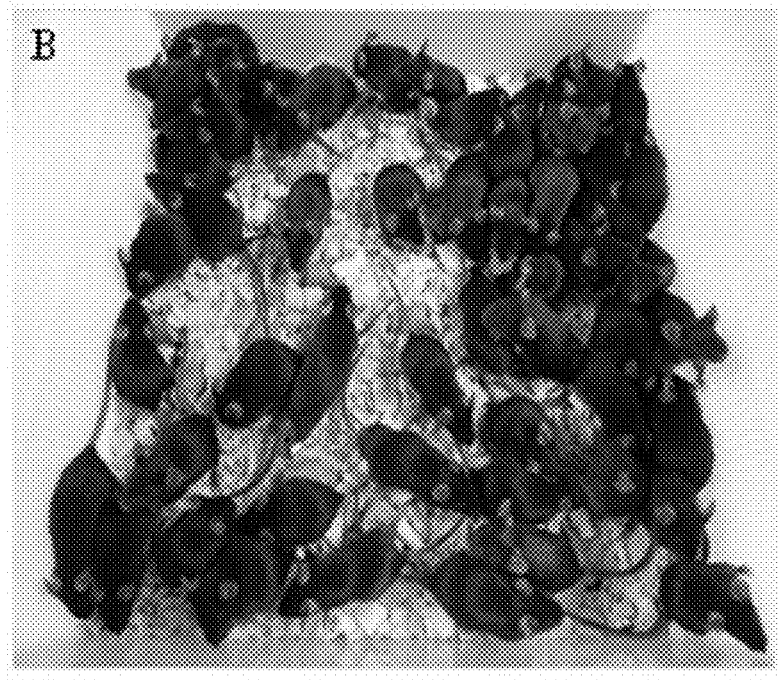
FIG. 3 is a photograph showing pups produced from one female mouse showing superovulation induced by administering IASe (0.1 mL of IAS and 3.75 IU of eCG) followed by administration of hCG.

As shown in Table 3, all recipients produced offspring from ovulated ova obtained by superovulation by IASe, after embryonic transplantation. The produced children are shown in FIG. 3. That is, offspring were obtained from fresh or cryopreserved embryos obtained by superovulation using IASe. There was no difference in the litter rate between the eCG treatment and the IASe treatment in any group of fresh or cryopreserved ova. The number of offspring from a female mouse superovulated with IASe was about 3-fold as compared with the eCG treatment.

(2-4) Investigation of Age in Weeks of Ovum Donor −1

Figure 4:
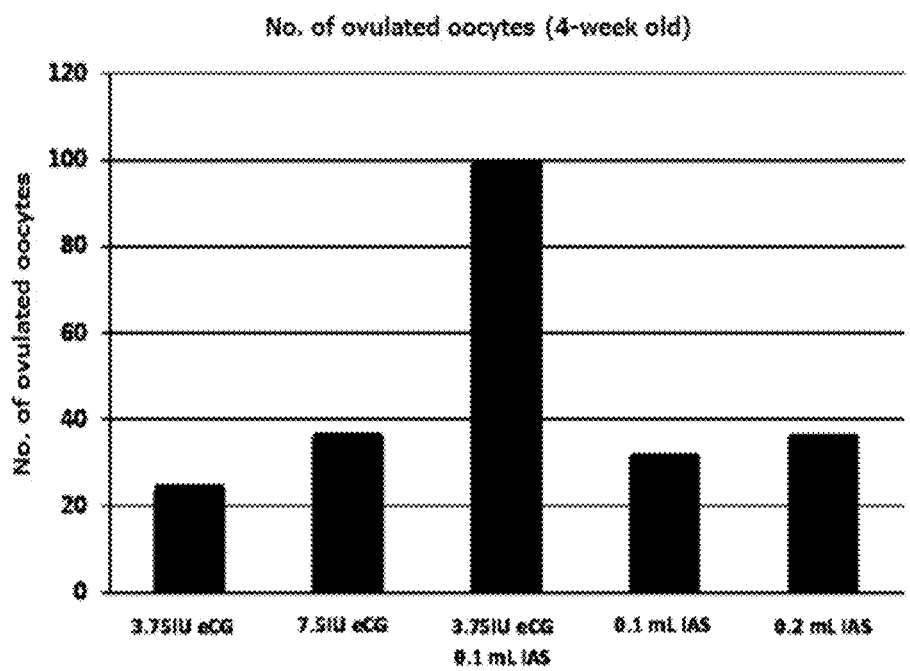
FIG. 4 shows the number of ovulated ova obtained by inducing superovulation using a 4-week old C57BL/6 female mouse. The results of the number of ova obtained by administering 3.75 or 7.5 IU of eCG alone, 0.1 mL or 0.2 mL of IAS alone, or IASe (0.1 mL of IAS and 3.75 IU of eCG), respectively, then, administering hCG, are shown.
Figure 5:
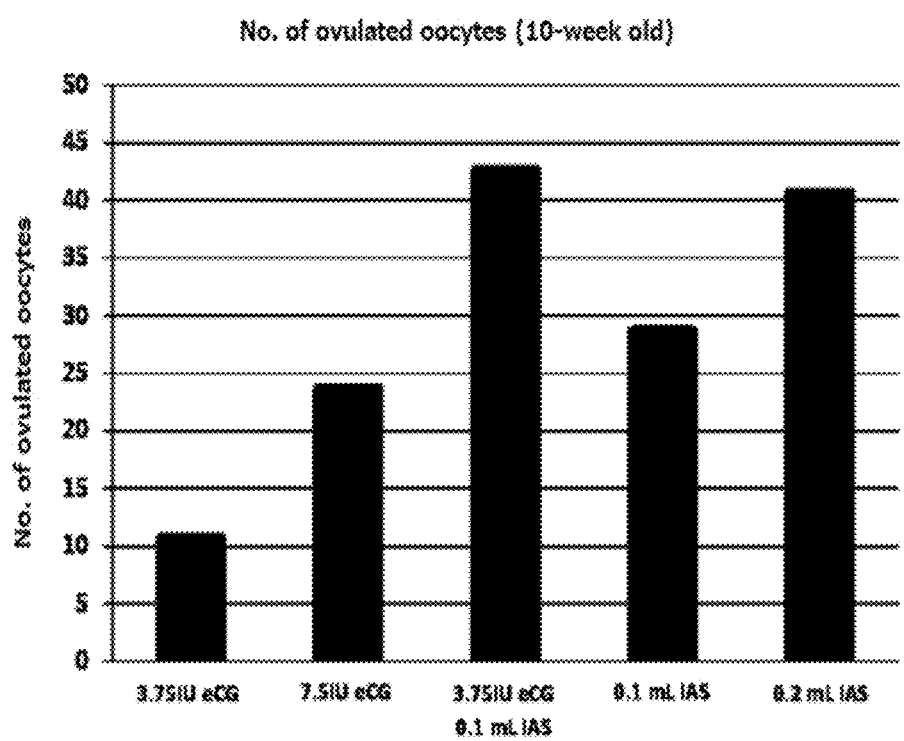
FIG. 5 shows the number of ovulated ova obtained by inducing superovulation using a 10-week old C57BL/6 female mouse. The results of the number of ova obtained by administering 3.75 or 7.5 IU of eCG alone, 0.1 mL or 0.2 mL of IAS alone, or IASe (0.1 mL of IAS and 3.75 IU of eCG), respectively, then, administering hCG, are shown.

Three kinds of administrations of IAS alone (0.1 mL or 0.2 mL), eCG alone (3.75 IU or 7.5 IU) and IASe (combination of IAS and eCG: 0.1 mL of IAS and 3.75 IU of eCG) were conducted using 4-week old and 10-week old female mice, and the ability of inducing superovulation was examined, in the same manner as in (2-1). The results are shown in FIG. 4 and FIG. 5.

Superovulation was remarkably induced in 4-week old mice as compared with 10-week old mice.

(2-5) Investigation of Age in Weeks of Ovum Donor −2

Figure 6:
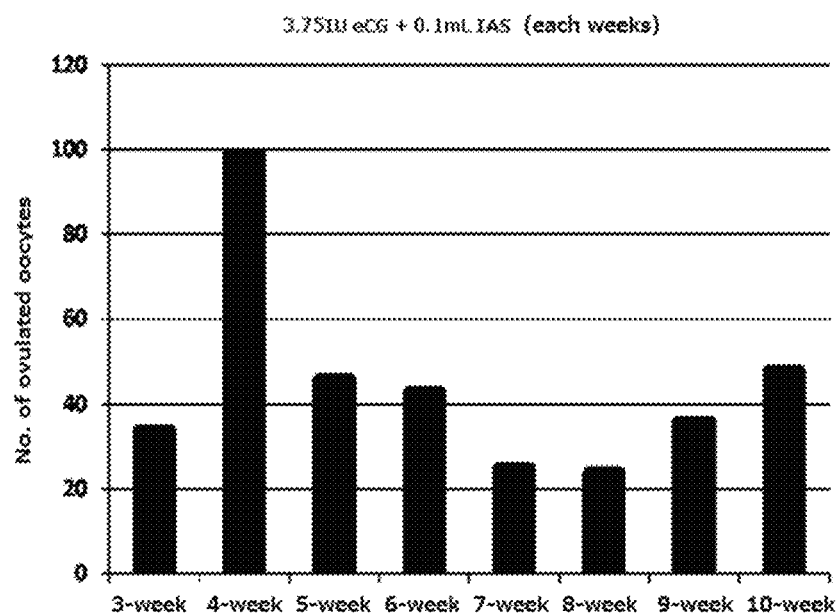
FIG. 6 shows results of induction of superovulation using C57BL/6 female mice of each weeks of age (3 to 10-week old). For superovulation, IASe (0.1 mL of IAS and 3.75 IU of eCG) were administered, then, hCG was administered.

Administration of IASe (combination of IAS and eCG: 0.1 mL of IAS and 3.75 IU of eCG) was conducted using 3-week old to 10-week old female mice, and the ability of inducing superovulation was examined, in the same manner as in (2-1). The results are shown in FIG. 6.

(2-6) Investigation of Combined Administration of IAS and eCG

An influence of the administration ratio in combined administration of IAS and eCG exerted on the ovulation number was investigated.

Figure 7:
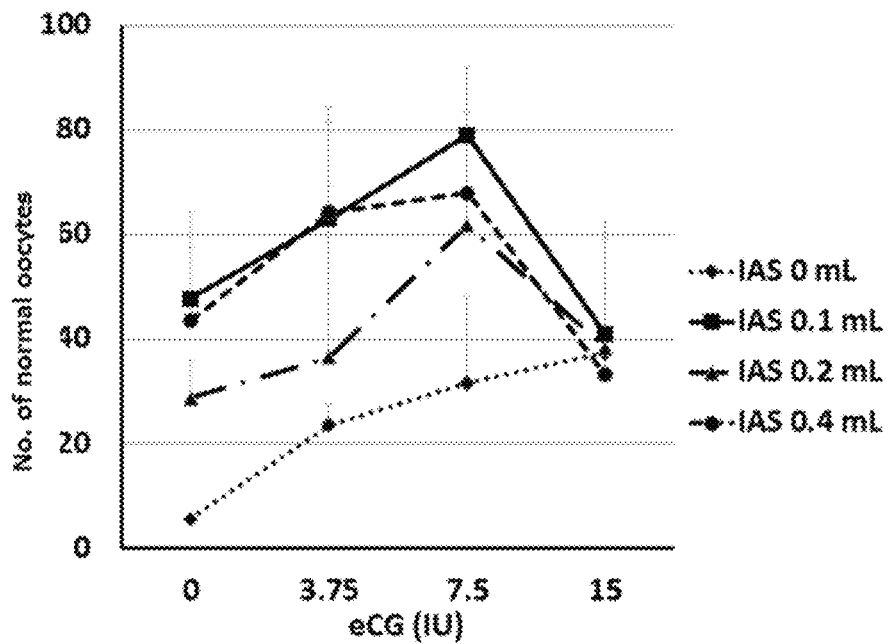
FIG. 7 shows results of induction of superovulation using a 4-week old C57BL/6 female mouse. For superovulation, respective dosages of IASe and eCG were administered, then, hCG was administered. At each condition, tests were conducted using 4 to 10 mice, and a statistical treatment was performed.
Figure 8:
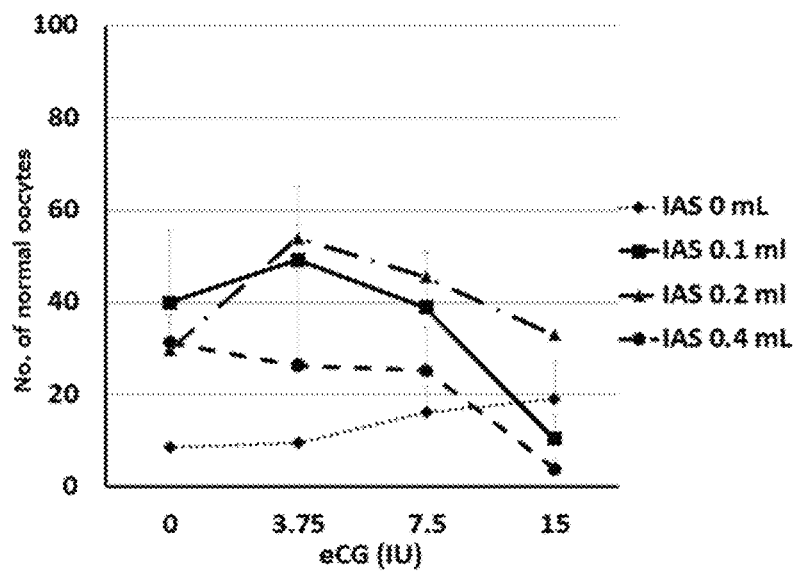
FIG. 8 shows results of induction of superovulation using 10 to 19-week old C57BL/6 female mice. For superovulation, respective dosages of IASe and eCG were administered, then, hCG was administered. At each condition, tests were conducted using a total of 3 mice of 12 weeks and 16 weeks of age, and a statistical treatment was performed.

In the same manner as in (2-1), 4-week old and 10 to 19-week old female mice were used, the administration ratio of IAS and eCG was changed, and the ability of inducing superovulation was examined. IAS was administered in an amount of 0 mL, 0.1 mL, 0.2 mL and 0.4 mL. eCG was administered in an amount of 0 IU, 3.75 IU, 7.5 IU and 15 IU. The results using 4-week old mice are shown in FIG. 7 and the results using 10 to 19-week old mice are shown in FIG. 8.

As understood from the results, an excellent superovulation induction effect is obtained by a combination of IAS and eCG, and combinations of 0.1 mL or 0.2 mL of IAS and 3.75 or 7.5 IU of eCG showed a particularly remarkable ovulation induction effect.

Figure 9:
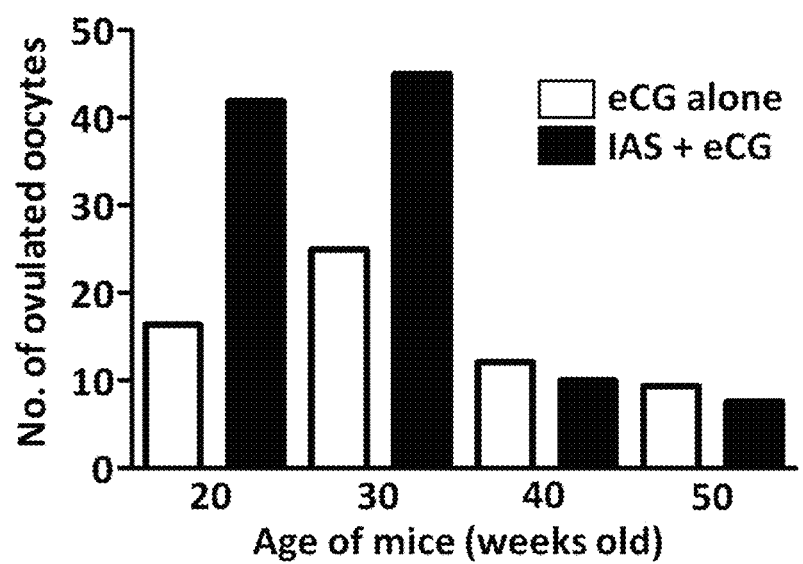
FIG. 9 shows the number of ovulated ova obtained by inducing superovulation using 20-week old to 50-week old C57BL/6 female mice. The results of the number of ova obtained by administering eCG (3.75 IU) alone and a combination of IAS (0.1 mL) and eCG (3.75 IU), respectively, then, administering hCG, are shown. At each condition, tests were conducted using 3 to 5 mice of respective weeks of age, and a statistical treatment was performed.

(2-7) Investigation of Combined Administration of IAS and eCG for 20-Week or Older Female Mouse The ability of inducing superovulation by a combination of IAS and eCG was examined using 20-week old, 30-week old, 40-week old and 50-week old female mice, in the same manner as in (2-1). eCG (3.75 IU) was administered alone, and IASe (0.1 mL of IAS and 3.75 IU of eCG) were administered. The results are shown in FIG. 9. Also in 30-week old female mice, an excellent ovulation induction effect was shown by a combination of IAS and eCG.

Figure 10:
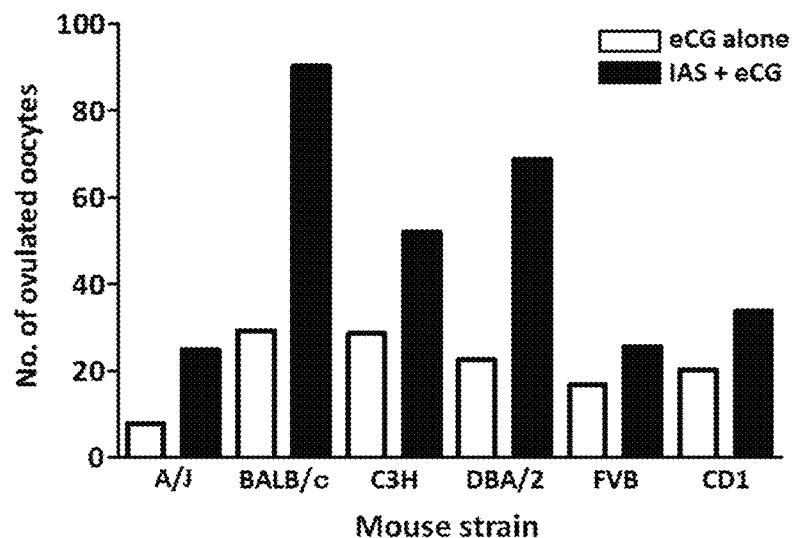
FIG. 10 shows the number of ovulated ova obtained by inducing superovulation using mice of various strains (4-week old). The results of the number of ova obtained by administering eCG (3.75 IU) alone and a combination of IAS (0.1 mL) and eCG (3.75 IU), respectively, then, administering hCG, are shown. At each condition, tests were conducted using 3 to 6 mice of respective strains, and a statistical treatment was performed.

(2-8) Investigation of Combined Administration of IAS and eCG for Mice of Various Strains The ability of inducing superovulation by a combination of IAS and eCG was examined using 4-week old female mice of various strains (A/J, BALB/c, C3H, DBA/2, FVB and CD1), in the same manner as in (2-1). eCG (3.75 IU) was administered alone, and IASe (0.1 mL of IAS and 3.75 IU of eCG) were administered. The results are shown in FIG. 10. Also in female mice of any strain, an excellent ovulation induction effect was shown by a combination of IAS and eCG.

(2-9) Investigation of Combined Administration of IAS and eCG at Low Dosage

Figure 11:
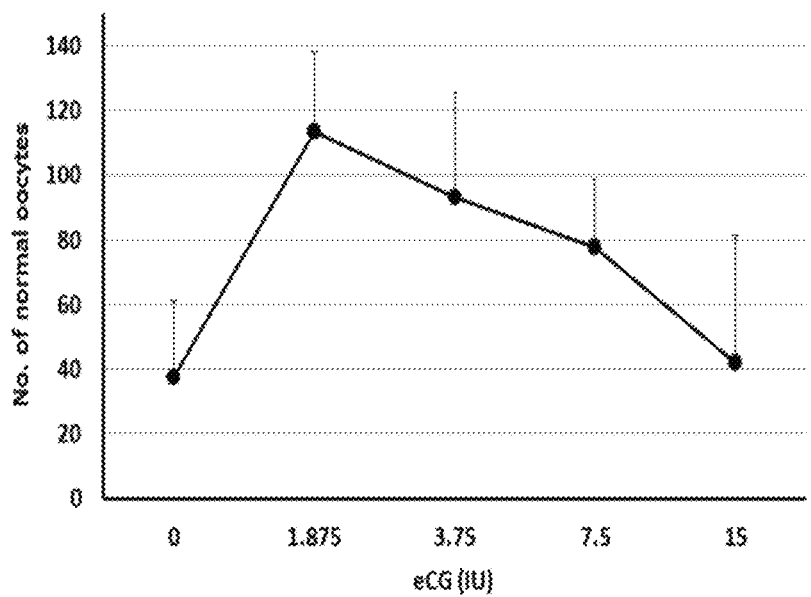
FIG. 11 shows the number of ovulated ova obtained by inducing superovulation using a low dosage of IAS (0.05 mL) using a 4-week old C57BL/6 female mouse. The results of the number of ova obtained by administering a combination of IAS and each amount of eCG (0 IU to 15 IU), then, administering hCG, are shown. At each condition, tests were conducted using 3 to 5 mice, and a statistical treatment was performed.

The ability of inducing superovulation by a combination of IAS and eCG at low dosage was examined using 4-week old female mice, in the same manner as in (2-1). IAS (0.05 mL) was administered alone, and a combination of IAS (0.05 mL) and 1.875 IU, 3.75 IU, 7.5 IU or 15 IU of eCG was administered. The results are shown in FIG. 11. Also when IAS was used at a low dosage of 0.05 mL, an excellent ovulation induction effect was shown by a combination of IAS and eCG.

According to the above-described results, it was shown that combined administration of IAS and eCG significantly increases the number of ovulated ova of a female mouse (particularly, C57BL/6 female mouse) as compared with the superovulation treatment using eCG or IAS alone. Further, the IASe treatment did not give a negative effect on the fertilization rate of an ovulated ovum. In addition, offspring were obtained normally from fresh or cryopreserved two-celled embryos produced by IVF between sperm of a genetically engineered mouse and ova of a female mouse using the IASe treatment. The present invention is a novel superovulation inducing method using IASe which stably produces a lot of ova from female mice of various strains. Particularly, the present invention is the first invention which stably produces over 80 ova and over 30 offspring from a single female mouse of C57BL/6 strain, and is a novel superovulation inducing method using IASe.

Superovulation is an important technology for efficiently obtaining ova from an ovum donor in experimental animals. In superovulation of a mouse, eCG is administered to a female mouse intraperitoneally, then, 48 hours after administration of eCG, hCG is administered in the same manner. Then, 14 to 17 hours after administration of hCG, ova are collected. This technique has been widely accepted as a standard method of superovulation, since the protocol was established. The present inventors showed that administration of 0.05 to 0.4 mL of IAS increases the number of ovulated ova like administration of 7.5 IU of eCG. Interestingly, combined administration of IAS and eCG to a female mouse (particularly, C57BL/6 female mouse) remarkably increased the number of ovulated ova. An improvement in the superovulation technique enables efficient production of ova and animals, and is useful for improvement of the experimental efficiency using a genetically engineered mouse.

C57BL/6 is known to belong to *Mus musculus domesticus*. The present inventors showed that responsiveness to IAS (0.05 to 0.4 mL) and responsiveness to eCG (7.5 IU) are equivalent in superovulation of a C57BL/6 strain female mouse. Further, the present inventors showed that responsiveness to IAS and responsiveness to eCG are amplified remarkably by administering them in combination. A novel administration method of a combination of IAS and eCG is a method effective for female mice of various strains, therefore, this administration method can increase the number of ovulated ova of wild-derived strains, irrespective of the genetic background.

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The technology of the present invention minimizes the number of female mice as an ovum donor, coincides completely with the rule of 3Rs, and conforms to the practice standard of animal tests. An improvement in the animal production efficiency by the superovulation inducing technique of the present invention is extremely useful for efficiency of researches in institutes around the world and mouse resource banks which can strongly promote the study of genome science using a genetically engineered mouse.

What is claimed is:

1. A superovulation inducing method, comprising simultaneously administering to a female mouse (a) anti-inhibin antibody and equine chorionic gonadotropin (eCG), (b) followed by human chorionic gonadotropin (hCG).

2. The superovulation inducing method according to claim 1, wherein the anti-inhibin antibody is administered in the form of inhibin antiserum.

3. The superovulation inducing method according to claim 2, wherein the female mouse is a 3 to 30-week old female mouse.

4. The superovulation inducing method according to claim 3, wherein the female mouse is 3 to 5 weeks of age.

5. The superovulation inducing method according to claim 4, wherein the female mouse is a C57BL/6 strain female mouse.

6. The superovulation inducing method according to claim 5, wherein the dosage of the inhibin antiserum is 0.4 mL or less.

7. The superovulation inducing method according to claim 6, wherein the dosage of the inhibin antiserum is between 0.05 mL and 0.4 mL.

8. The superovulation inducing method according to claim 7, wherein the dosage of the equine chorionic gonadotropin is between 1 IU and 10 IU.

9. The superovulation inducing method according to claim 2, wherein the dosage of the inhibin antiserum is between 0.05 mL and 0.4 mL.

10. The superovulation inducing method according to claim 1, wherein the female mouse is a 3 to 30-week old female mouse.

11. The superovulation inducing method according to claim 1, wherein the female mouse is a C57BL/6 strain female mouse.

12. The superovulation inducing method according to claim 1, wherein the dosage of the equine chorionic gonadotropin is between 1 IU and 10 IU.

13. An in vitro fertilization method comprising
    (i) a step of producing an oocyte and/or ovum using the method according to claim 1, and
    (ii) a step of fertilizing the oocyte and/or ovum produced by step (i) with sperm from a genetically engineered mouse.

14. The in vitro fertilization method according to claim 13, wherein the sperm is derived from a C57BL/6 strain male mouse.

* * * * *